(12) United States Patent
Hoffman

(10) Patent No.: US 6,700,948 B2
(45) Date of Patent: Mar. 2, 2004

(54) LOW-COST, MULTISLICE CT DETECTOR WITH MULTIPLE OPERATING MODES

(75) Inventor: David M. Hoffman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 247 days.

(21) Appl. No.: 09/735,008

(22) Filed: Dec. 12, 2000

(65) Prior Publication Data

US 2002/0071517 A1 Jun. 13, 2002

(51) Int. Cl.⁷ .............................................. G01N 23/00
(52) U.S. Cl. ..................................... 378/19; 250/370.09
(58) Field of Search ......................... 378/19; 250/370.09

(56) References Cited

U.S. PATENT DOCUMENTS

| | | | |
|---|---|---|---|
| 4,442,489 A | * | 4/1984 | Wagner ........................ 378/20 |
| 5,592,523 A | * | 1/1997 | Tuy et al. ..................... 378/19 |
| 5,799,057 A | | 8/1998 | Hoffman et al. |
| 5,974,109 A | | 10/1999 | Hsieh |
| 6,087,665 A | | 7/2000 | Hoffman et al. |
| 6,115,448 A | | 9/2000 | Hoffman |
| 6,134,301 A | | 10/2000 | Mruzek et al. |
| 6,137,857 A | | 10/2000 | Hoffman et al. |
| 6,144,718 A | | 11/2000 | Hoffman et al. |
| 6,173,031 B1 | | 1/2001 | Hoffman et al. |
| 6,198,791 B1 | | 3/2001 | He et al. |

OTHER PUBLICATIONS

International Search Report, dated Sep. 23, 2003, Application No. EP 01 31 0282, 3 pages.

* cited by examiner

Primary Examiner—Craig E. Church
(74) Attorney, Agent, or Firm—Carl B. Horton, Esq.; Armstrong Teasdale LLP

(57) ABSTRACT

One aspect of the present invention is a detector array for a computed tomographic imaging system having a z-direction corresponding to an image slice thickness direction and that is arc-shaped in a direction transverse to the z-direction. The detector array has a plurality of detector modules configured so that the detector array has active regions of differing thicknesses.

This detector array embodiment provides an optimized detector array for certain imaging situations, for example, in cardiac imaging applications in which increased coverage is required only in a relatively small central portion of a field of view.

11 Claims, 6 Drawing Sheets

LOW-COST, MULTISLICE CT DETECTOR WITH MULTIPLE OPERATING MODES

BACKGROUND OF THE INVENTION

This invention relates generally to detectors for computed tomography (CT) imaging systems, and more particularly to optimizations of such detectors for medical and other applications and to imaging systems using such optimized detectors.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. In another mode of operation of the CT imaging system, a helical scan is used to obtain projection data for images.

More particularly, and referring to FIGS. 1 and 2, one known computed tomograph (CT) imaging system embodiment 10 includes a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. In at least one embodiment of the present invention, detector array 18 is fabricated in a multi-slice configuration. Each detector element 20 produces an electrical signal that represents the intensity of an impinging x-ray beam. As the x-ray beam passes through a patient 22, the bean is attenuated. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Multiple slice detector arrays 18 increase the rate at which a scan of a given volume can be performed by acquiring data for several parallel image slices at the same time. For example, and referring to FIGS. 3 and 4, one known prior art detector array 18 includes a plurality of detector modules 50. Each detector module includes an array of detector elements 20. Particularly, each x-ray detector module 50 includes a plurality of scintillators 52 positioned above and adjacent corresponding photodiodes 54, a semiconductor device 56, and at least one flexible electrical cable 58. Photodiodes 54 are either individual photodiodes or a multi-dimensional photodiode array. Photodiodes 54 are optically coupled to scintillators 52 and generate electrical outputs on lines 60, wherein the outputs are representative of light output by corresponding scintillators 52. Each photodiode 54 produces a separate electrical output 60 that is a measurement of the beam attenuation for a specific element 20. Photodiode output lines 60 are, for example, physically located on one side of module 50 or on a plurality of sides of module 50. As shown in FIG. 4, photodiode outputs 60 are located at top and bottom of the photodiode array.

Semiconductor device 56 includes two semiconductor switches 62 and 64. Switches 62 and 64 each include a plurality of field effect transistors (FET) (not shown) arranged as a multidimensional array. Each FET includes an input line electrically connected to a photodiode output 60, an output line, and a control line (not shown). FET output and control lines are electrically connected to flexible cable 58. Particularly, one-half of photodiode output lines 60 are electrically connected to each FET input line of switch 62 with the remaining one-half of photodiode output lines 60 electrically connected to the FET input lines of switch 64.

Flexible electrical cable 58 includes a plurality of electrical wires 66 connecting its ends. FET output and control lines are electrically connected to cable 58. Particularly, each FET output and control line is wire bonded to a wire 66 of one end of cable 58. FET output and control lines are wire bonded to wires 66 in the same manner as photodiode outputs (not shown) are wire bonded to the FET input lines (also not shown). Cables 58 are secured to detector module 50 using mounting brackets 68 and 70.

Referring to FIG. 5, after mounting detector modules 50 into detector array 18, unconnected cable 58 ends are coupled to DAS 32 so that an electrical path exists between photodiode 52 outputs and DAS 32, and so that FET control lines 72 are electrically connected to DAS 32 to enable semiconductor device FETs 74. In a four-slice CT imaging system 10 using the prior art detector array 18 embodiment of FIGS. 3, 4, and 5, each column of detector module 50 is electrically connected to four DAS 32 channels, i.e., two channels within each flexible electrical cable 58. (In general, an N channel system would have N channels connected to each column of detector module 50, with N/2 channels within each flexible electrical cable 58.) One exemplary channel is represented, in part, in FIG. 5. DAS 32 is coupled across a rotating gantry 12 slip ring 76 to computer 36 and image reconstructor or processor 34. Each detector element 20 includes a photodiode 54 that is coupled to a plurality of FETs 74, only one of which is shown. In a four-slice CT imaging system, each channel is coupled to the output of one-fifth of FETs 74. (Of the FETs not shown in FIG. 5, one set connects unused diode elements to ground during a scan.) Computer 36 provides a control signal instructing a controller 78 to turn on one or more FETs 74 per channel per data interval during an imaging scan, resulting in an analog signal from a corresponding one or more photodiodes 54 being applied to a preamp 82. The output signal from preamp 82 is converted to a digital signal by analog to digital converter 84 and sent across slip ring 76 to image reconstructor 34.

For reconstruction of medical images without motion artifacts, it is desirable to rotate gantry 12 as rapidly as possible to obtain a set of views for image reconstruction. It is correspondingly desirable to sample the outputs of photodiodes 54 as rapidly as possible to obtain images with as high a resolution as possible. However, the highest sampling rate is limited by the bandwidth of data communication across slip ring 76, among other things. In some applications, it is desirable to image as large an extent in the z-direction as possible in as little time as possible. For these applications, it has been necessary to effectively combine outputs of detector elements 20 in adjacent rows of detector array 18 transverse to the z-direction by turning on more than one FET 74 at a time. This combination allows a greater extent of a patient to be imaged in the z-direction in a shorter time, but the reconstructed images correspond to thicker slices of the imaging volume in the z-direction (i.e., lower z-axis resolution).

Detector elements 20 are only 1.25 mm in extent in the z-direction in one known detector array 18. Moreover, even though one known detector array 18 provides 16 rows of detector elements 20, one known imaging system 10 using such a detector array only provides sufficient DAS 32 electronics to process four image slices at a time. Therefore, cardiac imaging applications require either that a helical scan be performed or that multiple axial scans be performed, with table 46 being stepped between the axial scans. Providing more rows of detector elements 20 in detector modules 50 of detector array 18 would reduce the time needed to acquire data for a complete image of a patient's heart, but this advantage could be gained only at the expense of a much greater number of DAS 32 channels.

It would therefore be desirable to provide a multislice detector array optimized for one or more imaging applications, including medical imaging applications. It would also be desirable to provide an imaging system using such a detector array that had a reduced need for additional DAS channels and additional bandwidth.

BRIEF SUMMARY OF THE INVENTION

There is therefore provided, in one embodiment of the present invention, a detector array for a computed tomographic imaging system having a z-direction corresponding to an image slice thickness direction and that is arc-shaped in a direction transverse to the z-direction. The detector array has a plurality of detector modules configured so that the detector array has active regions of differing thicknesses.

This detector array embodiment provides an optimized detector array for certain imaging situations, for example, in cardiac imaging applications in which increased coverage is required only in a relatively small central portion of a field of view. Such detector array embodiments also reduce the number of detector acquisition system (DAS) channels and the corresponding bandwidth needed to process information from the detector array, because detector elements and their associated electronics are not provided where they are not needed.

Figure 8:
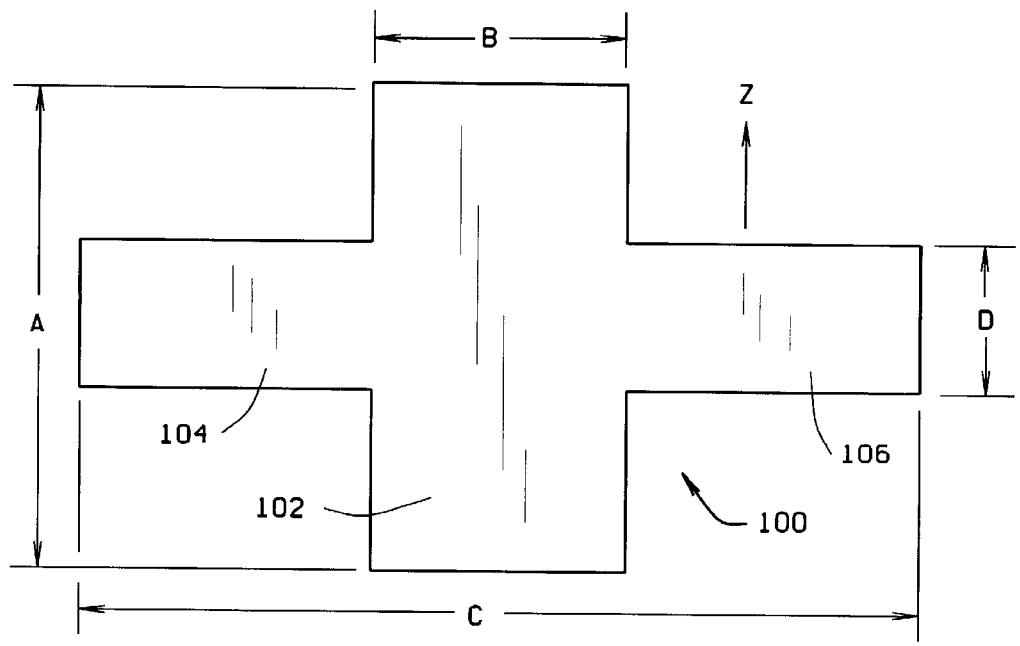
FIG. 8 is a simplified schematic representation of the "active" area of another embodiment of a multislice detector array of the present invention. The "active" area is that area covered by detector elements and facing the radiation source.

Detector elements are not shown. (The schematic representation of FIG. 8 is a projection of the active area onto a two-dimensional surface. The actual detector embodiment represented has a curvature similar to that shown in FIG. 6.)

Figure 9:
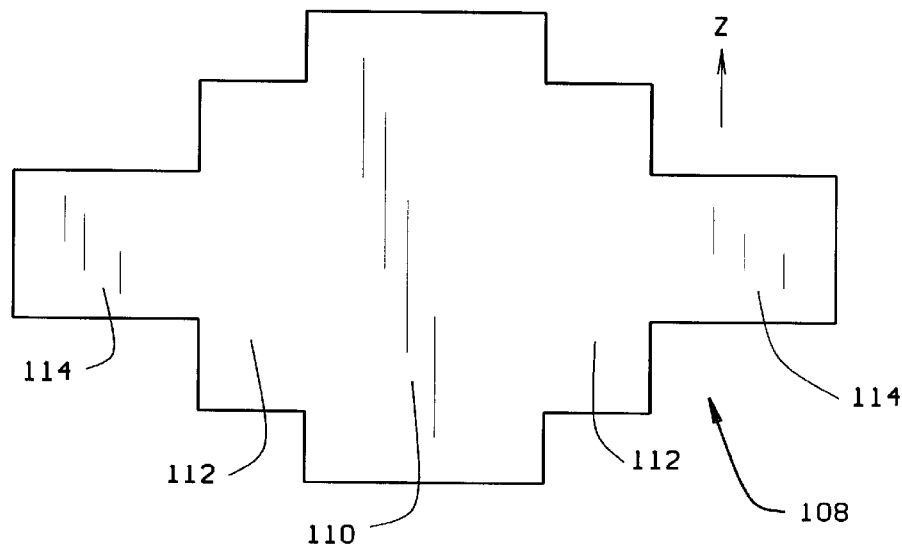

FIG. 9 is simplified schematic representation of another multislice detector array of the present invention.

DETAILED DESCRIPTION OF THE INVENTION

Figure 6:
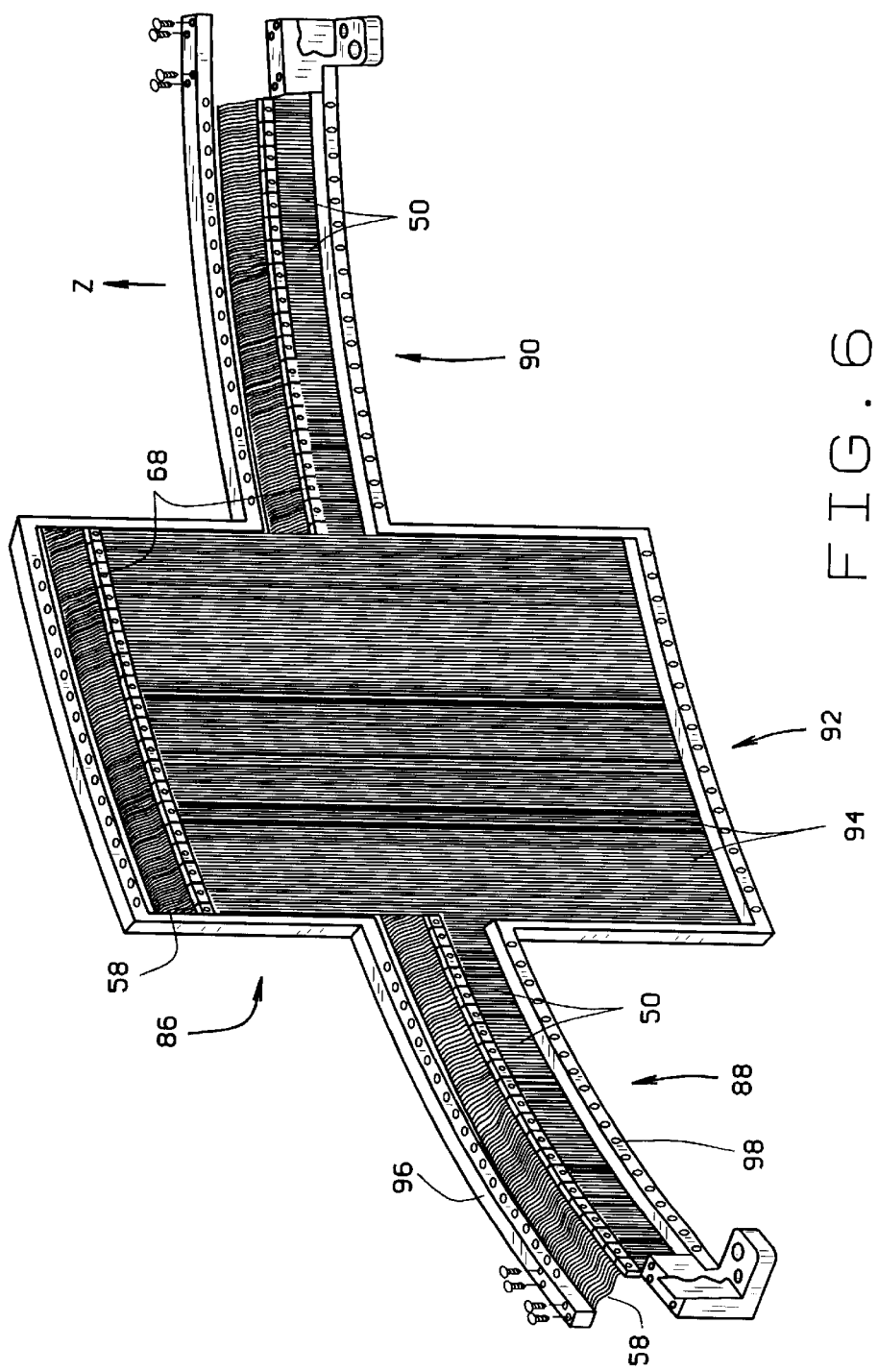
FIG. 6 is a perspective drawing of one embodiment of a multislice detector array of the present invention.
Figure 7:
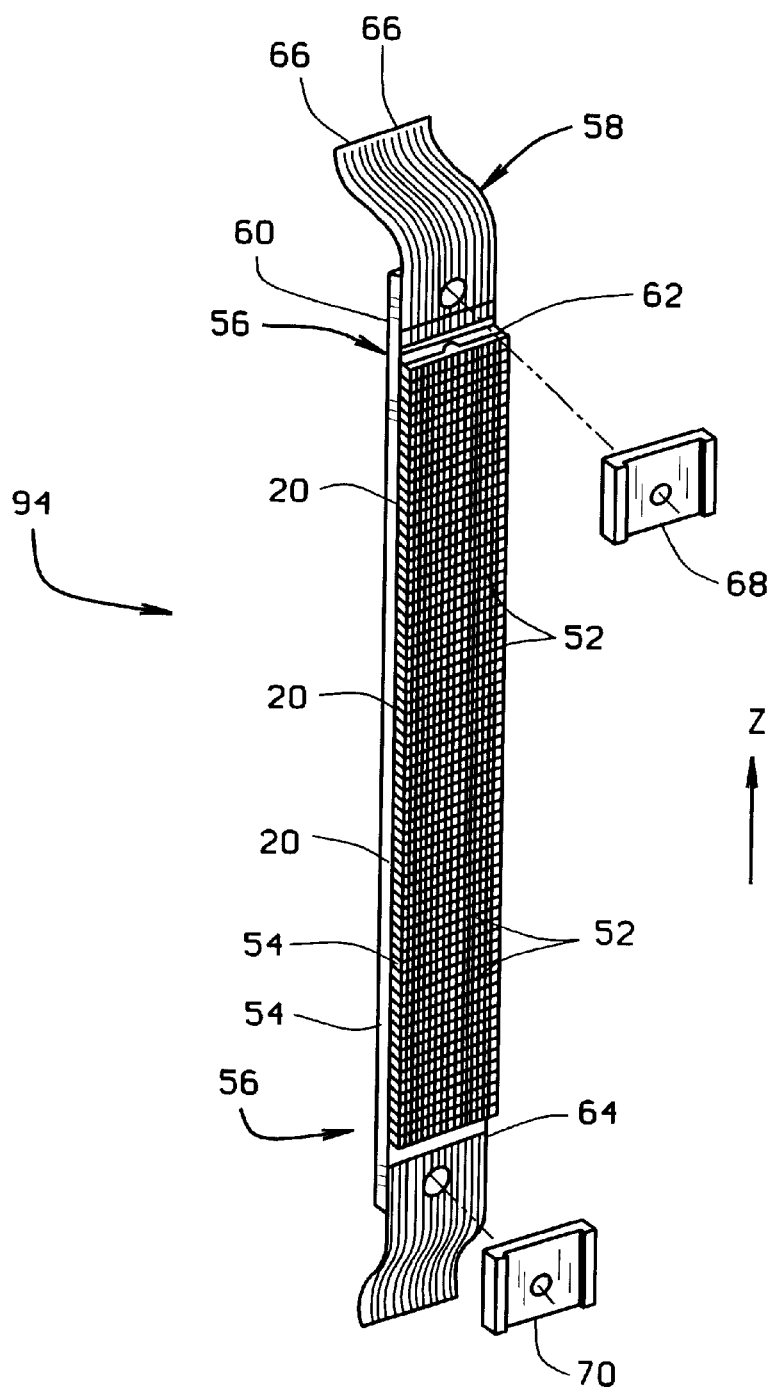
FIG. 7 is a perspective drawing of one representative type of detector module of the present invention useful for detector arrays of the type shown in FIG. 6.

In one embodiment of the present invention and referring to FIGS. 6 and 7, a detector array 86 is provided in place of detector array 18 of FIGS. 1–4 in a CT imaging system 10. Detector array 86 provides a first quantity of full field of view (FOV) slices for general body coverage, and a smaller FOV with a second, greater number of slices for more specialized scanning. Examples of specialized scanning include, but are not limited to, cardiac or other organ scanning, and head, neck, and limb scanning.

Detector array 86 comprises a plurality of different types of detector modules. Wings 88 and 90 utilize a first type of detector module, for example, the prior art detector module 50 of FIG. 4. A central region 92 utilizes a different type of detector module 94 of the present invention. For example, while detector modules 50 and 94 each comprise a rectangular array of detector elements 20, detector modules 94 provide a greater number of detector elements 20 in the z-direction (i.e., more detector rows) than do detector modules 50. To accommodate detector modules 94, rails 96 and 98 (or at least one of them) are shaped to provide a thick (i.e., large in the z-direction) "window" in the center of detector array 18. In one embodiment, to accommodate the additional detector elements 20 of detector module 86, multiple metal layers are used for the larger array of photodiodes 54, for semiconductor device 56 and/or for semiconductor switches 62 and 64. Also in one embodiment, flexible electrical cables 58 of detector modules 86 are multi-layer electrical cables.

Figure 1:
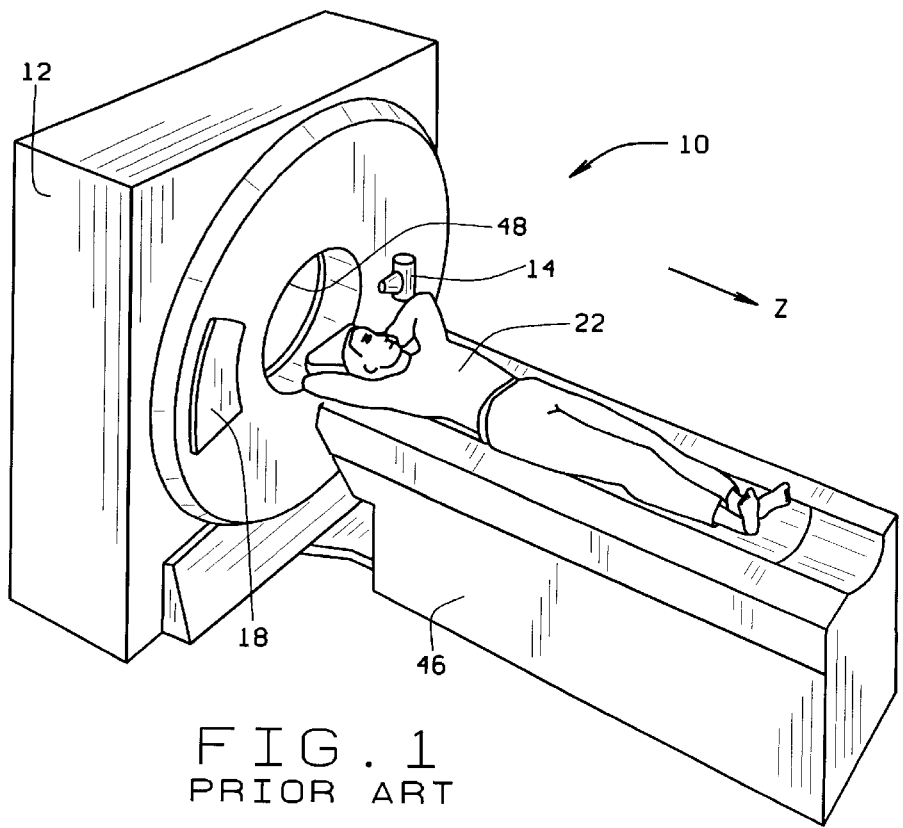
FIG. 1 is a pictorial view of a prior art CT imaging system.
Figure 2:
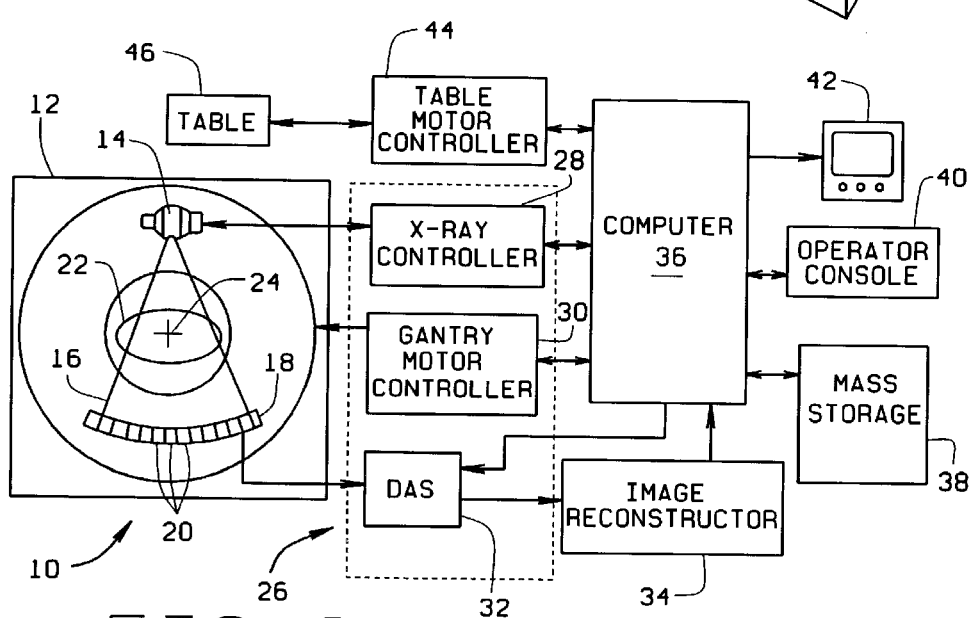
FIG. 2 is a block schematic diagram of the prior art system illustrated in FIG. 1.
Figures 3, 4:
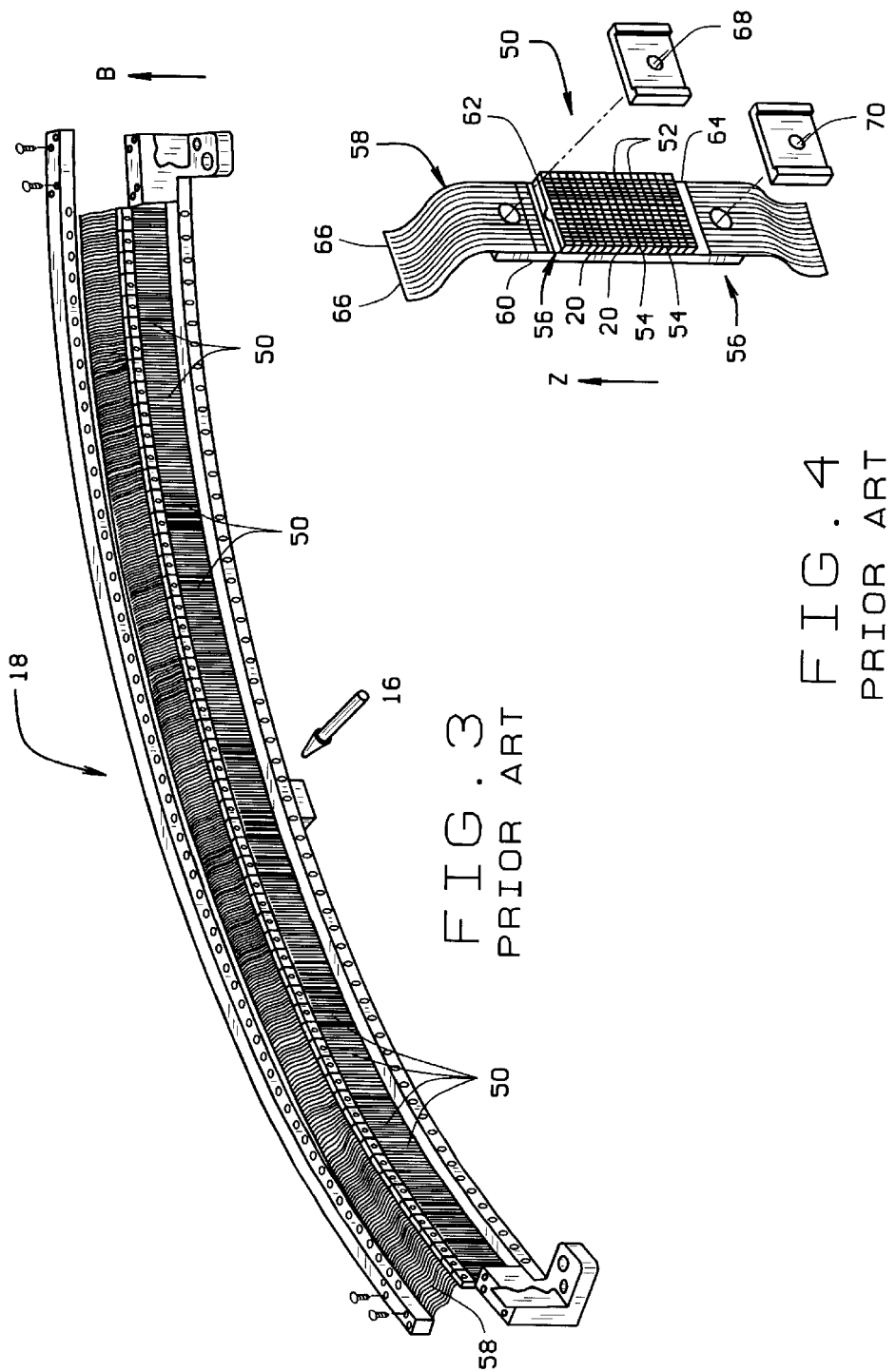
FIG. 3 is a perspective drawing of a prior art multislice detector array.
FIG. 4 is a perspective drawing of a prior art detector module of the detector array shown in FIG. 3.
Figure 5:
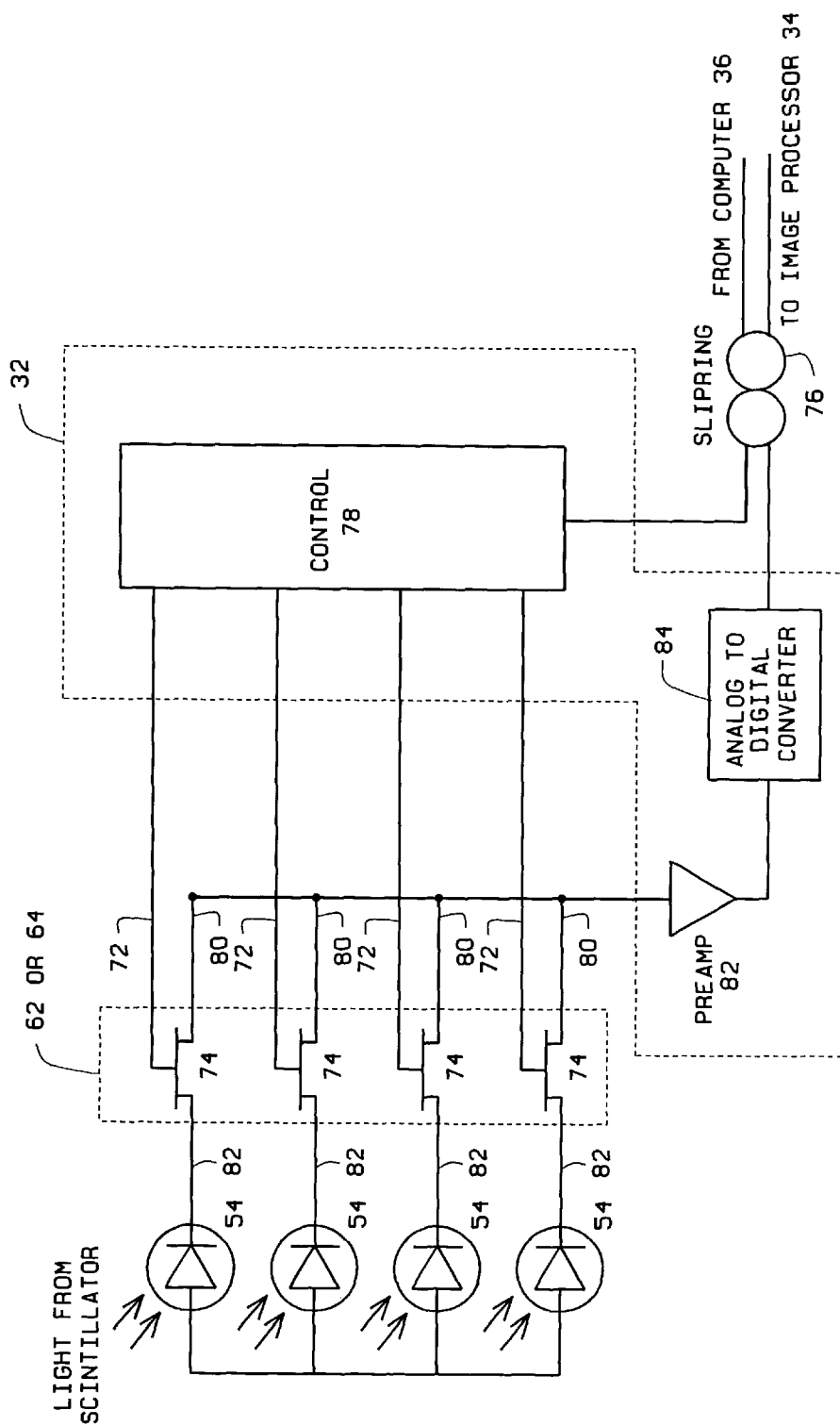
FIG. 5 is a simplified schematic diagram illustrating the concept of a DAS "channel."

Both the relative and absolute sizes of detector modules in wings 88 and 90 and those in central region 92 can be selected to provide embodiments providing specialized coverage for imaging. More particularly, embodiments of the present invention provide high resolution, large z-extent coverage in a selected portion or portions of detector array 86 where it is most useful for a particular application, for example, in central portion 92. Because a lesser coverage is provided elsewhere by detector array 86, extra DAS channels do not have to be provided for other regions of detector array 86 (e.g., wings 88 and 90.) To reduce the number of DAS 32 channels required, outputs of detector elements 20 are configurable for selective combination using FETs 74 (see FIG. 5). In one embodiment, the number of DAS 32 channels required is further reduced by utilizing different detector element 20 sizes to reduce resolution in some areas of detector array 86, for example, or by hard-wiring outputs of multiple detector elements 20 together.

In another embodiment of a detector array 100 of the present invention and referring to FIG. 8, the active area of detector 100 has a total dimension in the z-direction of 12 cm (dimension A). This thickness represents ninety-six parallel rows of detector elements 20 (not shown in FIG. 8) in a central region 102 that provides 16 cm of coverage (dimension B). Thus, detector modules (not shown in FIG. 8) in central region 102 have ninety-six detector elements in the z-direction. In one embodiment, detector modules in region 102 each have sixteen detector elements in a direction transverse to the z-direction, and fourteen modules are arranged adjacent one another in the direction transverse to the z-direction. These modules form central region 102 having the desired dimensions.

Wings 104 and 106 of detector array 100 allow detector array 100 to provide a FOV of 48 cm (dimension C). In the embodiment represented in FIG. 8, wings 104 and 106 comprise detector modules (not shown) having thirty two detector rows, and thus having a 4 cm extent in the z-direction (Dimension D). In one embodiment, each of these detector modules also has sixteen detector elements in a direction transverse to the z-direction and each wing 104, 106 comprises twenty-two modules adjoined in the direction transverse to the z-direction. These modules form wings 104, 106 having the desired dimensions.

In other embodiments, and referring to FIG. 9, a detector array 108 of the present invention comprises more than two sizes of detector modules, thus providing three (or more) regions 110, 112, 114 of different thicknesses in the z-direction. These additional embodiments provide FOVs optimized for other specialized types of scans. In some detector array embodiments, the thickest portion of the detector array is not necessarily in the center of the array, nor is the detector array itself necessarily symmetrical.

In summary, detector array embodiments of the present invention provide detector arrays having regions of unequal thicknesses in the z-direction. The dimension, locations, and numbers of regions are different in different embodiments, depending upon the type or types of scans for which the detector array and imaging system is specialized. However, in each case, the largest width FOV is not provided across the entire z-axis thickness of the detector array. Because a full FOV is not provided across the entire thickness of the detector array, it is also not necessary to provide DAS 32 channel circuitry to receive data for a full FOV of the detector array from each slice. Thus, both DAS 32 and detector array resources are optimized. Detector array embodiments of the present invention can be utilized in place of detector arrays 18 in conventional CT imaging systems such as imaging system 10 of FIGS. 1 and 2.

More particularly, sampling of analog outputs of detector elements 20 by DAS 32 proceeds at a frequency that is governed by speed and resolution requirements of imaging system 10. Outputs of detector elements 20 can be sampled separately. If lower resolution is acceptable, detector 20 outputs can be combined in pairs, for example, or in other combinations. In addition, sets of detector 20 outputs (or sets of combined detector 20 outputs) can be combined or multiplexed so that they share a single preamplifier 82 and analog-to-digital converter 84 of DAS 32.

In at least one embodiment of a detector array of the present invention, detector modules are tiled in two dimensions, one of which is the z-direction. In one embodiment, all of the tiled detector modules are the same size and have the same number of detector elements 20. Thicker regions of the detector array have more tiled detector modules in the z-direction than thinner regions.

While the invention has been described in terms of various specific embodiments, those skilled in the art will recognize that the invention can be practiced with modification within the spirit and scope of the claims.

What is claimed is:

1. A method for collecting data; said method comprising;
   scanning an object with a CT imaging system to generate imaging data, said CT imaging system comprising a detector ray having a z-direction corresponding to an image slice thickness direction and being arc-shaped in a direction transverse to the z-direction, said detector array comprising a plurality of detector modules configured so that said detector ray lies active regions of differing thicknesses; said scanning an object comprising rotating the detector and an x-ray source one revolution;
   collecting the imaging data from the scan; and
   reconstructing an image of the object using the imaging data collected during the scan.

2. A method in accordance with claim 1 wherein said collecting the imaging data comprises collecting imaging data of a cardiac cycle during the scan.

3. A method in accordance with claim 1 wherein said scanning an object with a CT imaging system further comprises scanning an object with a detector array having a z-direction corresponding to an image slice thickness direction and being arc-shaped in a direction transverse to the z-direction, said detector array comprising a plurality of detector modules configured so that said detector array has active regions of differing thicknesses.

4. A method in accordance with claim 1 wherein said scanning an object with a CT imaging system further comprises scanning an object with a detector array including detector modules that are configurable to selectively combine outputs of detector elements.

5. A method in accordance with claim 1 wherein said scanning an object with a CT imaging system further comprises scanning an object with a detector array including at least three regions each having a different thickness in the z-direction.

6. A method in accordance with claim 1 wherein said scanning an object with a CT imaging system further comprises scanning an object with a detector array including detector modules that are all of one size and have the same number of detector elements, and wherein said detector modules are tiled in two dimensions to produce said active regions of differing thicknesses.

7. A method in accordance with claim 1 wherein said scanning an object with a CT imaging system further comprises scanning an object with a detector array including at least a first set of detector modules having a first number of detector elements and a second set of detector modules having a second number of detector elements different from said first number of detector elements.

8. A method in accordance with claim 7 wherein said scanning an object with a CT imaging system further comprises scanning an object with a detector array including detector modules comprising rectangular arrays of detector elements said first set of detector modules having a greater number of detector elements in the z-direction than said second set of detector elements.

9. A method in accordance with claim 1, wherein said scanning an object with a CT imaging system further comprises scanning an object with a detector array including a relatively thicker, central region and relatively thinner wings on each side of the central region.

10. A method in accordance with claim 9 wherein said scanning an object with a CT imaging system further comprises scanning an object with a detector array including a pair of rails configured to attach to said detector modules and to provide a thick window in said central region.

11. A method in accordance with claim 9 wherein said scanning an object with a CT imaging system further comprises scanning an object with detector array including a central region having a thickness of 12 cm, said wings have a thickness of 4 cm, and said detector array provides a total field of view (FOV) of 48 centimeters, including said wings.

* * * * *

UNITED STATES PATENT AND TRADEMARK OFFICE
CERTIFICATE OF CORRECTION

PATENT NO. : 6,700,948 B2
DATED : March 2, 2004
INVENTOR(S) : Hoffman

It is certified that error appears in the above-identified patent and that said Letters Patent is hereby corrected as shown below:

Column 6,
Lines 35 and 36, after "comprising a detector" delete "ray" and insert therefor -- array --.

Column 8,
Line 14, after "scanning an object with" insert therefor -- a --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,700,948 B2
APPLICATION NO. : 09/735008
DATED : March 2, 2004
INVENTOR(S) : Hoffman It is certified that error appears in the above-identified patent and that said Letters Patent is hereby corrected as shown below:

In Claim 1, column 6, line 40, delete "detector ray lies active" and insert therefore -- detector array has active --.

Signed and Sealed this

Twenty-second Day of May, 2007

JON W. DUDAS
*Director of the United States Patent and Trademark Office*